United States Patent [19]

Van Lier

[11] Patent Number: 4,806,210

[45] Date of Patent: Feb. 21, 1989

[54] H₂S AND ALCOHOL RECOVERY PROCESS

[75] Inventor: Frank M. Van Lier, Lyndhurst, Ohio

[73] Assignee: The Lubrizol Corporation, Wickliffe, Ohio

[21] Appl. No.: 95,963

[22] Filed: Sep. 11, 1987

[51] Int. Cl.⁴ .................. B01D 1/22; C07F 9/165
[52] U.S. Cl. ........................... 203/89; 203/91; 159/49; 423/563; 558/112; 558/146; 568/749; 568/913
[58] Field of Search .............. 203/89, 72, 88, 91; 558/146, 112; 568/913, 749; 423/563; 159/13.1, 6.2, 49, 2.1, 46; 202/236

[56] References Cited

U.S. PATENT DOCUMENTS

| | | | |
|---|---|---|---|
| 2,514,944 | 7/1950 | Ferris et al. | 203/89 |
| 2,890,155 | 6/1959 | Beuche | 203/89 |
| 2,932,614 | 4/1960 | Lynch et al. | 558/146 |
| 3,201,331 | 8/1965 | Hunter | 203/89 |
| 3,225,817 | 12/1965 | Thier | 203/89 |
| 3,428,530 | 2/1969 | Fauche et al. | 203/89 |
| 3,573,293 | 3/1971 | Wiese | 558/146 |
| 4,020,129 | 4/1977 | Roszinski et al. | 558/146 |
| 4,185,053 | 1/1980 | Mirviss et al. | 558/140 |
| 4,198,276 | 6/1977 | Johnson et al. | 203/6 |
| 4,209,471 | 6/1980 | Dube | 558/150 |
| 4,263,103 | 4/1981 | Johnson et al. | 203/88 |
| 4,263,150 | 4/1981 | Clason et al. | 252/32.7 E |
| 4,308,154 | 12/1981 | Clason et al. | 252/32.7 E |

FOREIGN PATENT DOCUMENTS 1171385  11/1969  United Kingdom ............... 558/146

OTHER PUBLICATIONS

Chemical Abstracts: *Organophosphorus Compounds Reaction of Phosphorus Sulfides with Alcohols*, Kabachnik et al, 9909a, Oct. 1953, vol. 47, No. 19.

Widmer & Giger–"Residence Time Control in Thin-Film Evaporators", 11/19/70, Chem. & Process Eng.

"Agitated Thin-Film Evaporators", 9-13-65, Chemical Engineering.

*Primary Examiner*—Wilbur Bascomb
*Attorney, Agent, or Firm*—Forrest L. Collins; William C. Tritt; Roger Y. K. Hsu

[57]  ABSTRACT

A process for the recovery of alcohols and hydrogen sulfide from a thiophosphate containing mixture is disclosed.

44 Claims, No Drawings

H₂S AND ALCOHOL RECOVERY PROCESS

BACKGROUND OF THE INVENTION

1. Field of the Invention

The present invention describes a process for removing alcohols from a mixture of thermally sensitive organic phosphorus-containing agents. Hydrogen sulfide is also removed in this process.

2. Introduction to the Invention

It is known from U.S. Pat. No. 4,263,150, issued Apr. 21, 1981 to Clason et al that sulfur-containing salts of phosphorus acids may be prepared. Similar processing to obtain dialkylphosphorodithioic acid salts is found in U.S. Pat. No. 4,308,154 also to Clason issued Dec. 29, 1981. The sulfur-containing salts of dialkylphosphorodithioic acids are typically prepared by contacting a material such as phosphorus pentasulfide with an alcohol corresponding to the alkyl group in the dialkylphosphorodithioic acid. Typically, the alcohol is used in excess and is carried throughout the reaction and eventually recovred following the conversion of the dialkylphosphorodithioic acid to a corresponding metal salt. Hydrogen sulfide is present in the initial reaction mixture as a by-product.

The preparation of the metal salts of the dialkylphosphorodithioic acids involves the generation of water. The neutralization of the dialkylphosphorodithioic acid with, for example, zinc oxide results in the generation of water from the neutralization reaction. Steam treatment of the reaction mixture is also employed to assist in the stripping of excess alcohol. However, the water then contaminates the stripped alcohol. The effect of the steam processing is to further introduce water to the reaction mixture. Thus, the neutralization of the dialkylphosphorodithioic acids and the steam treatment amount to about 5 parts of water per 100 parts of the salt.

The presence of the water, from whatever source, the alcohol, and hydrogen sulfide present various processing difficulties. Any excess alcohol will be difficult to strip from the water. Where azeotropic conditions exist, it will not be possible without undue difficulty to remove the residual alcohol from the water. Conversely, the problem also exists in that some of the water which is bound to the alcohol is likely to remain in the alcohol following stripping. As the largest use of the dialkylphosphorodithioic salts is in lubricants, it is undesirable to have any water carried into the end product. The lower alcohols which are normally water-miscible and processed as described herein may be directly recycled to the reactor to generate more dialkylphosphorodithioic acid. Water wet lower alcohols may not be reused and are not commercially dryable. Excess hydrogen sulfide gas can result in zinc sulfide being formed thereby causing an inorganic salt to be present as well as loss of conversion to the desired zinc salt.

It has been proposed for the recovery of polycyclic alcohols to employ a thin-film evaporator. The foregoing technology is reported in U.S. Pat. No. 4,263,103 to Johnson et al issued Apr. 21, 1981. Similar technology with regard to thermally stabilizing alcohols is found in U.S. Pat. No. 4,198,276 issued June 24, 1977. Dube, in U.S. Pat. No. 4,209,471, issued June 24, 1980, states that a liquid-liquid extraction method is preferable to using a thin film or batch distillation process because of product stability and high vacuum requirements.

Various devices are known for use in thin film evaporation of organic materials. Such equipment is described in a reprinted article entitled "Residence Time Control in Thin-Film Evaporators" by Widmer and Giger which was originally printed in *Chemical and Process Engineering*, Nov. 19, 1970. A further disclosure of evaporation techniques and equipment is found in an article entitled "Agitated Thin-Film Evaporators" originally published in *Chemical Engineering*, Sept. 13, 1965.

Ordinarily, the processing of oil soluble components in a thin-film evaporator is conducted on materials which are extremely viscous or even solid at room temperature (20° C.). In the present invention, the dialkylphosphorodithioic acids and excess alcohols which are processed according to the invention are normally liquid materials at temperatures of −40° C.

The present invention deals with the separation of excess alcohol from dialkylphosphorodithioic acids prior to the neutralization of the acid to the corresponding salt. Blowing with dry nitrogen to enhance water removal may be avoided. Water contamination of the alcohol is avoided. Steam treatment to remove higher alcohols is avoided. Hydrogen sulfide gas is separated and may be recovered. The formation of zinc sulfide is avoided herein. Water haze in the end product is also minimized.

Throughout the specification and claims, percentages and ratios are by weight, temperatures are in degrees Celsius and pressures are in KPa gauge unless otherwise noted. Ratios and percentages herein are exemplary and may be combined. To the extent that the references cited herein are relevant to the present invention, they are herein incorporated by reference.

SUMMARY OF THE INVENTION

The present invention describes a process for recovering alcohols from a mixture of the alcohol and a phosphorus compound of the formula:

where $R^1$ and $R^2$ are each aliphatic or aromatic groups, wherein the mixture is preheated to a temperature of about 20° C. to about 115° C., and thereafter rapidly adjusting the mixture to a temperature of about 80° C. to about 180° C. for a period of time sufficient to substantially separate the alcohol from the phosphorus compound without the substantial generation of hydrogen sulfide.

A further aspect of the invention is a process for removing hydrogen sulfide from a mixture of the hydrogen sulfide and a phosphorus compound of the formula:

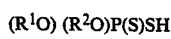

where $R^1$ and $R^2$ are each aliphatic groups containing from 1 to about 10 carbon atoms, wherein the mixture is pre-heated to a temperature of about 20° C. to about 115° C., and thereafter rapidly adjusting the mixture to a temperature of about 80° C. to about 180° C. for a period of time sufficient to substantially separate the hydrogen sulfide from the phosphorus compound without the substantial generation of additional hydrogen sulfide.

DETAILED DESCRIPTION OF THE INVENTION

The di-substituted phosphorodithioic acids of the present invention are prepared in the following manner. To prepare a di-substituted dithiophosphoric acid of the formula $(R^1O)(R^2O)P(S)SH$, a material such as phosphorus pentasulfide is condensed with an alcohol. The values of $R^1$ and $R^2$ are the hydrocarbyl residue of the alcohol. In the present invention, $R^1$ and $R^2$ are each conveniently aliphatic or aromatic groups or mixtures of the two.

In the course of reacting the phosphorus pentasulfide with the alcohol, it is convenient to use an excess of the alcohol to ensure complete formation of the reaction product. Typically, an excess of 10% to 1%, preferably not more than 20% of the alcohol is utilized over the stoichometric weight amount required to prepare the di-substituted dithiophosphoric acid. The alcohol is conveniently removed herein at 1% to 20% levels in the mixture. The removal of the alcohol is effective, at about 80% to 100% by weight of the excess alcohol originally present.

The alcohols which may be utilized in the present invention may be of any chain length, however, the alcohols are preferably aliphatic, most preferably alkyl. The alcohols as a preferred source of $R^1$ and $R^2$ in the present invention are branched or straight chain alcohols having from 1 to about 10, preferably 3 to about 8 carbon atoms. Particularly preferred values for $R^1$ and $R^2$ are from the use of isopropyl alcohol, isooctyl alcohol, amyl alcohol, isobutyl alcohol, methylpentyl alcohol, or 2-ethylhexyl alcohol. Aromatic groups which may be utilized include phenol, creosol or alkylated phenols, typically those containing from about 1 to about 15 carbon atoms in the alkyl portion of the alkyl phenol.

The essence of the present invention is to treat a mixture of a phosphorus compound as described in the Summary of the Invention and the excess alcohol and/or the hydrogen sulfide to a temperature from about 20° C. to about 115° C., preferably from about 28° C. to about 110° C., thereafter rapidly adjusting the mixture to a temperature of 80° C. to 180° C., preferably about 105° C. to about 160° C. In the use of the term "adjusting", it is generally understood that the adjustment of the temperature will be upward and will be done on as rapid a basis as is possible. It is within the equipment parameters of the present invention, however, to adjust the temperature to a lower temperature and to utilize vacuum conditions in the preferred equipment aspect of the invention described below to obtain the separation of the alcohol and/or hydrogen sulfide from the phosphorus compound.

The preferred equipment for use in the present invention is either a thin film evaporator or a wiped film evaporator. The basic difference between a thin film evaporator and a wiped film evaporator is that the latter scrapes the walls of the evaporator substantially clean of the product whereas the thin film evaporator while using a blade leaves a thin film of the material on the walls of the evaporator. Either the thin film evaporator or the wiped film evaporator may be utilized in the present invention with a preference toward using the thin film evaporator. Both the thin film evaporator and the wiped film evaporator serve the additional function of agitating the product on the wall of the evaporator to effect a substantially complete removal of the alcohol and the hydrogen sulfide.

The excess alcohol from the present invention and/or the hydrogen sulfide are both valuable by-products. The alcohol may be recycled to prepare additional di-substituted dithiophosphates while the hydrogen sulfide may be utilized for other processes requiring this gas.

The following is a description of an agitated thin-film evaporator. Agitated thin-film evaporators are designed to spread a thin layer or film of liquid on one side of a metallic surface, with heat supplied to the other side. The unique feature of this equipment is not the thin film itself but rather the mechanical agitator device for producing and agitating the film.

This mechanical agitator permits the processing of high-viscosity liquids, liquids with suspended solids, or those requiring liquid rates too small to keep the thermal surface of, say, a falling-film evaporator uniformly wet (this condition is called surface starving). The agitation produces a complex liquid-flow pattern when compared to "standard" evaporators. The usual flow resulting from gravity or the pumping mechanism is greatly complicated by the action of agitator blades plowing through the liquid film. The film thickness is conveniently about 1.0 mm to about 5 mm, preferably about 1.25 mm to about 2.5 mm. The evaporator is typically constructed such that there are four non-scraping blades attached to a rotation shaft on the unit) rotating at a speed of 9.1 to 12.2 meters/second (30 to 40 ft./sec.), pushes a bow wave having a zone length determined by product properties and the vertical liquid flow rate. Zone lengths of 2.5 cm to 10.1 cm (1 to 4 in.) are typical. Adjacent to the bow wave is a highly turbulent "squeeze zone" followed by a "tranquilizing" zone; this three-stage cycle is repeated by the next blade attached to the vertical rotor.

Energy induced by the rotation blade is mainly consumed by internal friction or turbulence within the liquid. In commercial equipment, this energy is approximately 0.16 w/square cm to 0.32 w/square cm (150 to 300 w./sq. ft.). This is equivalent to the pressure drop of a liquid flowing at 3.66 to 7.31 meters/second (12 to 24 ft./sec.) through a 0.635 cm (¼ inch) I.D. tube with a surface of 929 square cm (1 sq. ft.). These comparable velocities are considerably higher than actual velocities in tube heat exchangers and explain the high heat-transfer values in agitated thin-film evaporators.

Agitation has benefits in thin-film equipment other than liquid turbulence. The blades assure even distribution of the liquid over the metal heat-transfer surface; they eliminate any channeling of liquid as the liquid flows down the evaporator; the considerable shearing effect decreases the apparent viscosity of the product, thus improving internal heat and mass transfer. Heat-transfer rates between the liquid and the wall, in most situations, determine the size and effectiveness of thin-film equipment.

In many applications, the low wall temperatures due to high film-side heat transfer rates is important. With temperature differences between the heating medium and the liquid of 80° C. to 100° C. the product-side wall temperature is usually only 10° C. to 20° C. above the liquid boiling temperature. By comparison, the falling-film evaporator may have a product-side temperature 20° C. to 40° C. above the boiling point in a similar situation with the possibility of hot-spots developing on the heat-transfer wall.

In many applications of the agitated thin-film evaporator, mass transfer, not heat transfer, determines size and capacity of the equipment. Deodorization, low-boiler stripping, and dehydration are mass-transfer-controlled processes. A volatile component has to be transported within the film to the interface, then vaporized. Transport of the volatile component within the film is accomplished by molecular diffusion or by eddy diffusion. Molecular diffusion, the only possibility in laminar flow, is extremely slow and decreases linearly with increasing viscosity of the film liquid. Eddy diffusion can be influenced and increased by adding turbulence to the film. Values of diffusivities in agitated thin-film evaporators are on the order of $10^{-6}$ sq. m./sec. or 1,000 to 10,000 times greater than molecular diffusivities.

The high heat-transfer rates in agitated thin-film units is an important advantage when carrying out chemical reactions in the equipment. The high specific heat-transfer area permits accurate control of the reacting temperature. Also, the high rates of mass transfer favor reactions that form a volatile reaction product since removal of the product shifts the reaction equilibrium toward further conversion of the desired material.

Countercurrent liquid-vapor flow in an agitated thin-film evaporator can produce a "reflux effect" that will increase stripping or fractionation efficiency. Cocurrent liquid-vapor flow is considered to eliminate this effect entirely. It should be noted that with an internal separator and condenser, the vapor and liquid streams are separated completely and this eliminates the reflux effect. Should there be entrained concentrated liquid in the vapor stream, the separator is designed to discharge it with the balance of the concentrated material. The "fractionation effect" of countercurrent liquid-vapor flow is approximately 0.25 to 0.5 theoretical plates better than the 1-plate efficiency of a straight distillation pot.

The residence time for the mixture of the alcohol and the phosphorus and/or hydrogen sulfide temperature at which the separation of the alcohol and/or hydrogen sulfide effected is typically from about 0.5 seconds to about 10 minutes, preferably from about 10 seconds to about 1 minute, and most preferably from about 12 seconds to about 25 seconds. The foregoing time at the later described pressure conditions typically will remove from about 80% to 100% by weight of the alcohol present in the mixture, preferably from about 85% to about 100% of the alcohol mixture which has been unreacted. Substantially complete removal of the hydrogen sulfide is also effected in the processing of the present invention. It is, of course, not desirable in the present invention to break down the phosphorus compounds to generate alcohol and/or additional hydrogen sulfide.

The application of a vacuum herein is typically in the range of about 0.26 KPa to 13.3 KPa (2 mm Hg-100 mm Hg), preferably from about 0.93 KPa to 4 KPa (7 mm Hg-30 mm Hg). It has been found that the application of the vacuum substantially increases the yield of the hydrogen sulfide and the unreacted alcohol. The use of vacuum allows the alcohol and hydrogen sulfide to be removed without further degradation of the phosphorus compounds.

There are five major producers of agitated thin-film equipment in the U.S.: Buflovak Div. of Blaw-Knox, Votator Div. of Chemetron, Luwa, Kontro, and Pfaudler.

The following is a suggested example of the present invention.

EXAMPLE I

A feed stream comprising diisooctyl dithiophosphoric acid, isooctyl alcohol, and hydrogen sulfide gas is obtained as previously described. The components are in a respective weight ratio of 91.8:8:0.2. This reaction mixture is maintained at a temperature of about 110° C.

A Luwa TM thin-film evaporator, model number L210-1600-15, is employed. The separation between the walls of the still and the rotor blade is set for 1.8 mm. The evaporator is set for a relatively even heat distribution system of 166° C. The evaporator is equipped for overhead take off for hydrogen sulfide and excess isooctyl alcohol. The diisooctyl dithiophosphoric acid, the excess isooctyl alcohol and the hydrogen sulfide are then charged to the evaporator at a rate of 3.3 kg/minute. The hydrogen sulfide is observed to distill rapidly from the 1.8 mm thick falling film of the composition. Substantially, all of the hydrogen sulfide is removed prior to the composition flow front reaching the midpoint of the still flow path. The excess isooctyl alcohol is substantially completely removed by the time the product reaches the sump in the evaporator. The evaporator is equipped such that the diisooctyl dithiophosphoric acid may be removed at the bottom and drawn off for further processing. At the point at which the diisooctyl dithiophosphoric acid is removed from the sump, it is found to be at a temperature of about 166° C. and is immediately cooled. No degradation of the diisooctyl dithiophosphoric acid is observed.

Substantially similar results are obtained with a variety of alcohols including 2-ethylhexyl, isobutyl, amyl or methylpentyl. A further variation of the present invention is to utilize a wiped film evaporator wherein there is substantially no space between the still wall and the scraping blade.

What is claimed is:

1. A process for recovering alcohols from a mixture of the alcohol and a phosphorus compound, of the formula:

$$(R^1O)(R^2O)P(S)SH$$

where $R^1$ and $R^2$ are each aliphatic or aromatic, wherein the mixture is preheated to a temperature of about 20° C. to about 115° C., and thereafter rapidly adjusting the mixture to a temperature of about 80° C. to about 180° C. for a period of time sufficient to substantially separate the alcohol from the phosphorus compound without the substantial generation of hydrogen sulfide.

2. The process of claim 1 wherein $R^1$ and $R^2$ each contain from about 1 to about 10 carbon atoms.

3. The process of claim 1 wherein the adjusting is rapid heating which is accomplished in from about 5 seconds to about 10 minutes.

4. The process of claim 1 wherein at least one of $R^1$ and $R^2$ is isooctyl.

5. The process of claim 1 wherein the preheating is to about 28° C. to about 110° C.

6. The process of claim 1 wherein at least one of $R^1$ and $R^2$ is amyl.

7. The process of claim 1 wherein adjusting of the mixture is rapidly heating to a temperature of about 105° C. to about 160° C.

8. The process of claim 1 wherein the mixture during adjusting is mechanically agitated.

9. The process of claim 1 wherein at least one of $R^1$ and $R^2$ is isobutyl.

10. The process of claim 1 wherein at least one of $R^1$ and $R^2$ is methylpentyl.

11. The process of claim 1 wherein the rapid adjusting step is conducted in a wiped film evaporator.

12. The process of claim 1 wherein the alcohol is present in the mixture at about 1% to about 20% by weight.

13. The process of claim 1 wherein $R^1$ and $R^2$ each contain from about 3 to about 8 carbon atoms.

14. The process of claim 1 wherein $R^1$ and $R^2$ are both aliphatic groups.

15. The process of claim 1 wherein the alcohols are selected from the group consisting of phenol, cresol and alkylated phenols and mixtures thereof.

16. The process of claim 1 wherein a vacuum is applied during the separation of the alcohol from the phosphorus compound.

17. The process of claim 1 wherein the adjusting is a rapid heating step is conducted on a falling film of the mixture.

18. The process of claim 17 wherein the falling film is about 1.25 to about 5 millimeters in thickness.

19. The process of claim 1 wherein at least one of $R^1$ and $R^2$ is 2-ethylhexyl.

20. The process of claim 3 wherein the rapid heating is from about 10 seconds to about 1 minute.

21. The process of claim 1 wherein the alcohol removed from the mixture during adjusting includes a rapid heating step wherein about 80% to about 100% by weight of the alcohol present in the mixture is removed.

22. The process of claim 1 wherein the rapid heating step is conducted in a thin film evaporator.

23. A process for removing hydrogen sulfide from a mixture of the hydrogen sulfide and a phosphorus compound of the formula:

where $R^1$ and $R^2$ are each aliphatic groups containing from 1 to about 10 carbon atoms, wherein the mixture is pre-heated to a temperature of about 20° C. to about 115° C., and thereafter rapidly adjusting the mixture to a temperature of about 80° C. to about 180° C. for a period of time sufficient to substantially separate the hydrogen sulfide from the phosphorus compound without the substantial generation of additional hydrogen sulfide.

24. The process of claim 23 wherein $R^1$ and $R^2$ each contain from about 1 to about 10 carbon atoms.

25. The process of claim 23 wherein the adjusting is by rapid heating which is accomplished in from about 5 seconds to about 10 minutes.

26. The process of claim 23 wherein at least one of $R^1$ and $R^2$ is isooctyl.

27. The process of claim 23 wherein the preheating is to about 28° C. to about 110° C.

28. The process of claim 23 wherein at least one of $R^1$ and $R^2$ is amyl.

29. The process of claim 23 wherein the adjusting of the mixture is by rapidly heating to a temperature of about 105° C. to about 160° C.

30. The process of claim 23 wherein the mixture during adjusting is mechanically agitated.

31. The process of claim 23 wherein at least one of $R^1$ and $R^2$ is isobutyl.

32. The process of claim 23 wherein at least one of $R^1$ and $R^2$ is methylpentyl.

33. The process of claim 23 wherein the adjusting is by rapid heating conducted in a wiped film evaporator.

34. The process of claim 23 wherein the adjusting is rapid heating conducted on a falling film of the mixture.

35. The process of claim 23 wherein at least one of $R^1$ and $R^2$ is 2-ethylhexyl.

36. The process of claim 23 wherein the rapid heating step is from about 10 seconds to about 1 minute.

37. The process of claim 23 wherein the rapid heating step is conducted in a thin film evaporator.

38. The process of claim 23 wherein $R^1$ and $R^2$ each contain from about 3 to about 8 carbon atoms.

39. The process of claim 23 wherein $R^1$ and $R^2$ are both aliphatic groups.

40. The process of claim 23 wherein the alcohols are selected from the group consisting of phenol, cresol and alkylated phenols and mixtures thereof.

41. The process of claim 23 wherein a vacuum is applied during the separation of the hydrogen sulfide from the phosphorus compound.

42. The process of claim 34 wherein the falling film is about 1.25 to about 5 millimeters in thickness.

43. The process of claim 1 wherein the alcohol is isopropanol.

44. The process of claim 23 wherein the alcohol is isopropanol.

* * * * *